United States Patent [19]

Goswami et al.

[11] Patent Number: 5,358,875
[45] Date of Patent: Oct. 25, 1994

[54] METHOD AND COMPOSITION FOR HALOHYDROCARBON DETECTION

[75] Inventors: Kisholoy Goswami; Dileep K. Dandge; Stanley M. Klainer, all of Henderson; Chuka H. Ejiofor, Las Vegas, all of Nev.

[73] Assignee: FIC - FiberChem, Inc., Las Vegas, Nev.

[21] Appl. No.: 82,248

[22] Filed: Jun. 25, 1993

[51] Int. Cl.⁵ .................. G01N 21/78; G01N 21/64
[52] U.S. Cl. ............................... 436/124; 436/165; 436/167; 436/169; 436/172; 436/902; 252/183.11
[58] Field of Search .............. 436/8, 18, 124, 125, 436/126, 163, 167, 169, 902, 172; 252/183.11, 964; 422/61

[56] References Cited

U.S. PATENT DOCUMENTS

| | | | |
|---|---|---|---|
| 4,847,428 | 7/1989 | Gu | 568/639 |
| 5,051,513 | 9/1991 | Jelich | 546/315 |
| 5,227,560 | 7/1993 | Clement et al. | 585/500 |

Primary Examiner—David A. Redding
Attorney, Agent, or Firm—Henry P. Sartorio

[57] ABSTRACT

A sensing chemistry for halogenated hydrocarbons includes pyridine or a pyridine derivative and a strong organic alkoxide base. The sensing chemistry may be in a nonaqueous organic solvent or in a solid state matrix. The base reacts with the halohydrocarbon to produce a carbene intermediate reaction product, which in the absence of water preferentially reacts with the pyridine to form a colored and/or fluorescent product.

18 Claims, 5 Drawing Sheets

METHOD AND COMPOSITION FOR HALOHYDROCARBON DETECTION

BACKGROUND OF THE INVENTION

The invention relates generally to the chemical detection of halogenated hydrocarbons (halohydrocarbons) and more particularly to the detection of halohydrocarbons, including certain organic chlorides, using a Fujiwara-like reaction.

Trichloroethylene (TCE) heads the U.S. Environmental Protection Agency's (EPA) list of hazardous (toxic, carcinogenic, etc.) compounds and the organic chlorides, as a group, dominate the ten (10) most frequently found dangerous compounds. The other organic chlorides include 1,1,1-trichloroethane (TCA), 1,1,2,2-tetrachloroethane, chloroform ($CHCl_3$), carbon tetrachloride ($CCl_4$) and 1,2-dichloroethylene (DCE). Thus, the detection of these compounds is extremely important.

The Fujiwara reaction is a known methodology widely used for the fluorometric and colorimetric analysis of gem-polyhalogen compounds. In the presence of a strong alkali ($OH^{31}$), such as sodium or potassium hydroxide, pyridine or a derivative thereof reacts with a halogenated hydrocarbon to produce a red colored fluorescent product. The traditional chemistry (pyridine/alkali metal base) is a two-phase system, since the commonly used alkalis (NaOH or KOH) in water are insoluble in pyridine. Therefore, the reaction product is formed only at the interface. The Fujiwara chemistry has been modified to overcome the limitations of the two-phase system. U.S. Pat. No. 4,929,562 to Anderson (deceased) et al. shows a single-phase system which utilizes pyridine or a derivative thereof with a hindered nitrogen base (phase transfer catalyst), particularly a tetraalkyl ammonium hydroxide (quaternary ammonium base). The larger bases (because of the larger cations) have increased solubility in pyridine so that a single phase is achieved. However, the bases are still inorganic bases, i.e., $OH^-$ is the base. The chemistry is not particularly compound specific but is species specific.

A major problem with the Fujiwara (pyridine/base) reaction is the problem of competing pathways for the carbene reaction intermediate. Water, the typical solvent for inorganic bases, consumes the carbene, thereby preventing completion of the preferred reaction with pyridine. Therefore, it is desirable to modify or improve the conventional Fujiwara chemistry to eliminate the problems of the prior art. Also, pyridine is an offensive-smelling hazardous material. Its derivatives, although not as bad as pyridine itself, are not soluble in water to an appreciable extent. Therefore, it is very important to develop a non-aqueous system in order to employ pyridine derivatives in place of pyridine. Also, liquid pyridine is not amenable to fabrication of a solid state sensor, so developing a pyridine derivative based system is also important for solid state applications.

SUMMARY OF THE INVENTION

Accordingly, it is an object of the invention to provide a sensing chemistry for halohydrocarbons which overcomes the deficiencies of the prior art Fujiwara reaction.

The invention is a detecting reagent composition or sensing chemistry for halogenated hydrocarbons. The composition is pyridine or a derivative thereof with an organic base, an alkoxide, in place of the inorganic bases used in the prior art Fujiwara chemistry. Suitable alkoxides include potassium tertiary butoxide (KTBO), sodium isopropoxide, titanium isopropoxide, aluminum isopropoxide, sodium ethoxide, and sodium methoxide. These alkoxides can have any suitable counterion (e.g., sodium, potassium, lithium, ammonium or transition metals). A nonaqueous organic solvent is used which dissolves the alkoxide but does not react with carbene like water does. Suitable solvents include tertiary butyl alcohol, acetonitrile, and tetrahydrofuran. A base modifier, e.g., a pyrimidine, can also be added. The base modifier is a weaker organic base that causes changes in the reaction product. Suitable base modifiers include pyrimidine, acetaldehyde-ammonia trimer, 1,5-diazabicyclo[4.3.0]non-5-ene, 1,4diazabicyclo[2.2.2]octane, 1,8-diazabicyclo[5.4.0]undec-7-ene. The sensing chemistry could be immobilized in a polymer or other suitable substrates like porous glass to produce a solid state sensor. In some cases, because of widely separated absorption peaks for different species, identification of the species is easy. In other cases, more complex spectroscopic analysis (chemometrics) is needed to distinguish the species. In other cases, different reaction times temporally separate the reaction products for different species.

DETAILED DESCRIPTION OF THE PREFERRED EMBODIMENTS

The sensing chemistry according to the invention is the combination of ( 1 ) an indicator or color forming reactant selected from pyridine and derivatives thereof, or other compounds that carbene can react with, and (2) a relatively strong organic base selected from an alkoxide, or other organic base that can react with the halohydrocarbon to form carbene, in ( 3 ) a nonaqueous solvent. The chemistry can also include (4) a base modifier, a weaker heterocyclic organic compound selected from pyrimidine, which alters the reaction product formed. The pyridine or pyridine derivative will react with an intermediate from a halogenated hydrocarbon to produce a colored product. The alkoxide base is preferably potassium tertiary butoxide (KTBO), but others including isopropoxides, ethoxides, and methoxides, etc. with counterions selected from sodium, potassium, lithium, ammonium, etc. can be used. The solvent is nonaqueous and nonreactive with the carbene intermediate product formed in the halohydrocarbon-base reaction. Suitable organic solvents include tertiary butyl alcohol, isopropyl alcohol, acetonitrile and tetrahydrofuran. The solvent must of course also dissolve the other components. The pyrimidine base modifier is preferably hexahydro pyrimido pyrimidine (HPP) but also includes hexahydro methyl pyrimido pyrimidine (HMPP).

The invention produces a different reaction product than produced by the conventional Fujiwara chemistry.

Figure 1:
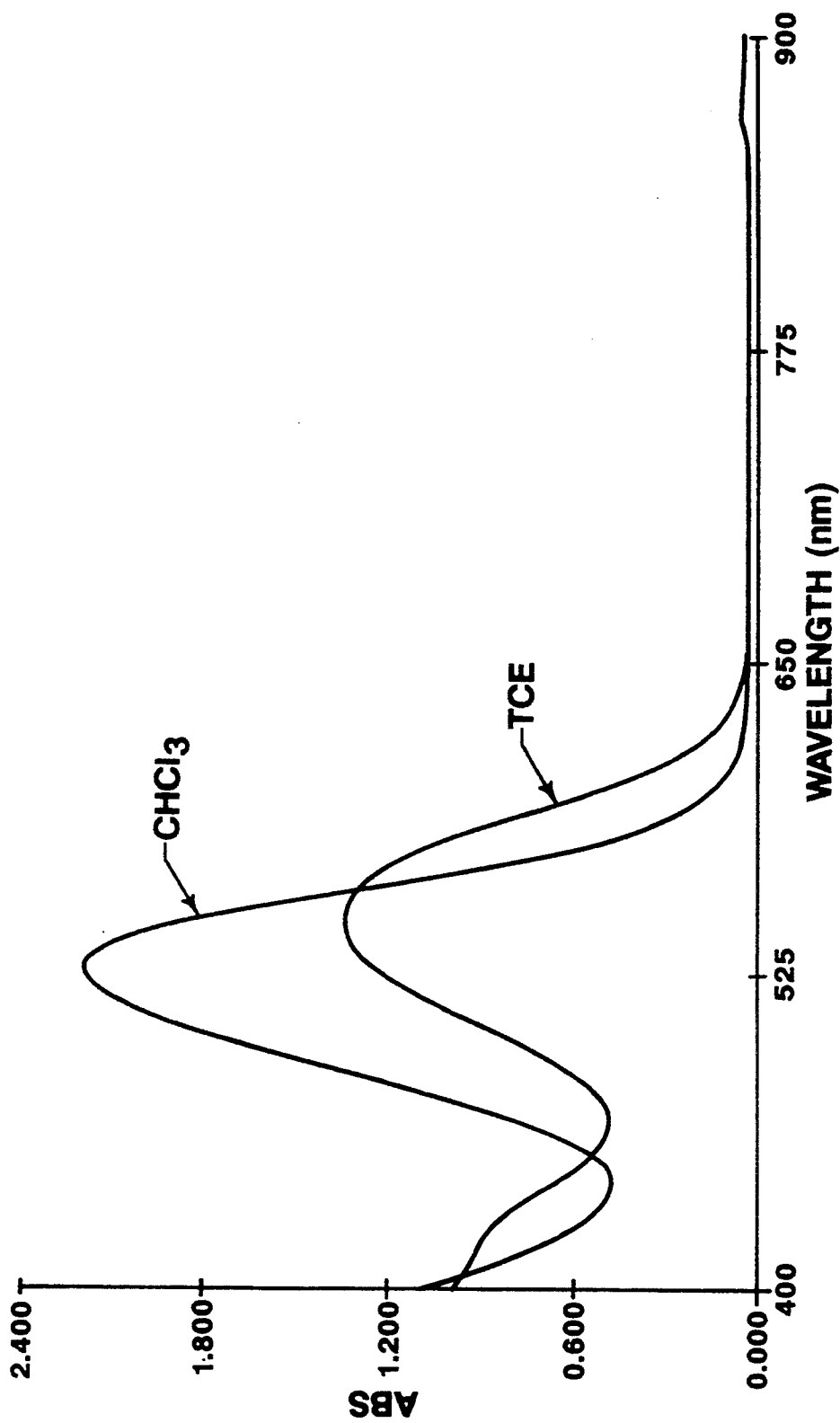
FIG. 1 shows the absorption spectrum for chloroform and TCE using a prior art Fujiwara chemistry.
Figure 2:
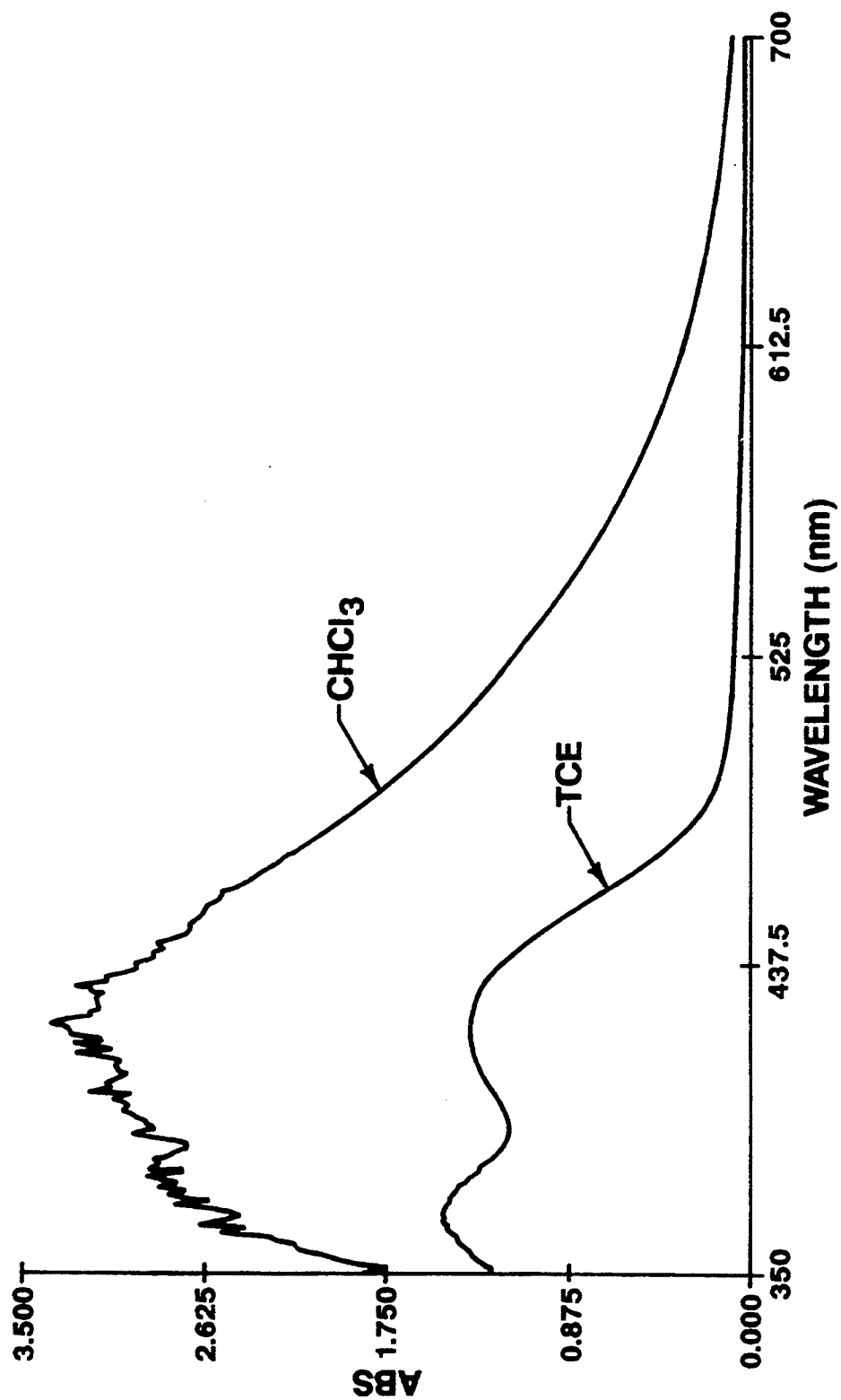
FIG. 2 shows the absorption spectrum for chloroform and TCE using 4,4'-bipyridine and KTBO in tertiary butyl alcohol.

FIG. 1 shows the results for two halohydrocarbons, chloroform and TCE, using a Fujiwara chemistry of 65% pyridine, and 35% aqueous tetrabutylammonium hydroxide. The absorption spectra for both halohydrocarbons have absorption bands between about 500–600 nm with peaks at about 525–550 nm; thus the two compounds cannot be differentiated. FIG. 2 shows the results for the same two halogenated hydrocarbons using a chemistry of 4,4'-bipyridine (5% wt./vol.) and KTBO (1N) in tertiary butyl alcohol. The peaks of the absorption spectra again significantly overlap, making identification difficult, but the peaks are at totally different wavelengths, in the band about 350–450 nm, than the products shown in FIG. 1.

The invention operates by utilizing an organic base B where $B^-$ is the base anion (e.g. alkoxide) on a halogenated hydrocarbon usually a geminal polyhalogenated hydrocarbon, having an active hydrogen, active meaning extractable by the base eventually leading to a carbene intermediate which then reacts with pyridine. The reactions are as follows:

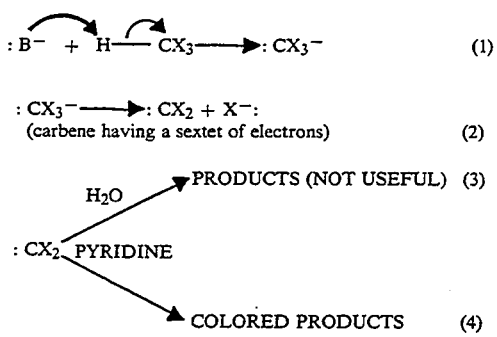

$$:B^- + H\text{—}CX_3 \longrightarrow :CX_3^- \quad (1)$$

$$:CX_3^- \longrightarrow :CX_2 + X^-: \quad (2)$$
(carbene having a sextet of electrons)

$$:CX_2 \underset{PYRIDINE}{\overset{H_2O}{\diagup\diagdown}} \begin{array}{l} \text{PRODUCTS (NOT USEFUL)} \quad (3) \\ \\ \text{COLORED PRODUCTS} \quad (4) \end{array}$$

where $HCX_3$ (X=halogen) is an illustrative halohydrocarbon.

In the first reaction (1), the halohydrocarbon reacts with the base anion. In the second reaction (2), the intermediate product carbene is formed. Reaction (4) is desired over reaction (3). If the solvent is water, then the undesired reaction (3) preferentially occurs unless there is a large excess of pyridine. However, by use of a nonaqueous solvent, reaction (4) preferentially occurs.

In more general terms, the sensing chemistry has a chromogenic or fluorogenic indicator and an intermediate generator in a solvent or support (substrate) with an optional base modifier. The intermediate generator is a strong base (i.e., a base that in water would have a pH>8 or more, preferably>12) which can abstract an active hydrogen (or other element) from the target analyte to generate a reaction intermediate, e.g. a carbene. The chromogenic/fluorogenic indicator is a compound, e.g., pyridine, with which the intermediate can react to produce a color change for absorption measurement and/or a product which can be monitored fluorometrically, by intensity or lifetime or polarization measurements. The base modifier is another compound having a heteroatom (atom other than C or H) which can modify the properties of any of the measurable product or intermediate, before, during or after the reaction. The solvent/support is passive and holds the active components together.

The organic bases are stronger and bulkier than the $OH^-$ used in the prior art, and they form a homogeneous mixture in the organic phase. However, the bases cannot be so strong that they will react with everything in the system, e.g., the solvent. They should react preferentially with the halohydrocarbons. Since they are bigger, the organic bases go into organic phase more easily, in either solution or solid state.

The base modifier is another organic base, but weaker than the alkoxide. Preferably the base modifier is a pyrimidine, such as HPP or HMPP.

The sensing chemistry can be used to form a solid state halohydrocarbon sensor. Although pyridine itself cannot be used because it is a liquid, various substituted pyridines (pyridine derivatives) which are solids can be used. The pyridine derivative and alkoxide are dissolved in the solvent along with an immobilization polymer. This formulation is cast on a suitable support or substrate. The solvent is then removed, e.g., by evaporation, to produce a solid state sensor with the sensing chemistry embedded in a polymer immobilization matrix. This chemistry can also be used on porous glass or similar material. The polymer must be sufficiently porous to allow the halohydrocarbon to enter the matrix; a plasticizer can be added to increase permeability.

The following are examples of specific compositions.

EXAMPLE 1

Figure 3:
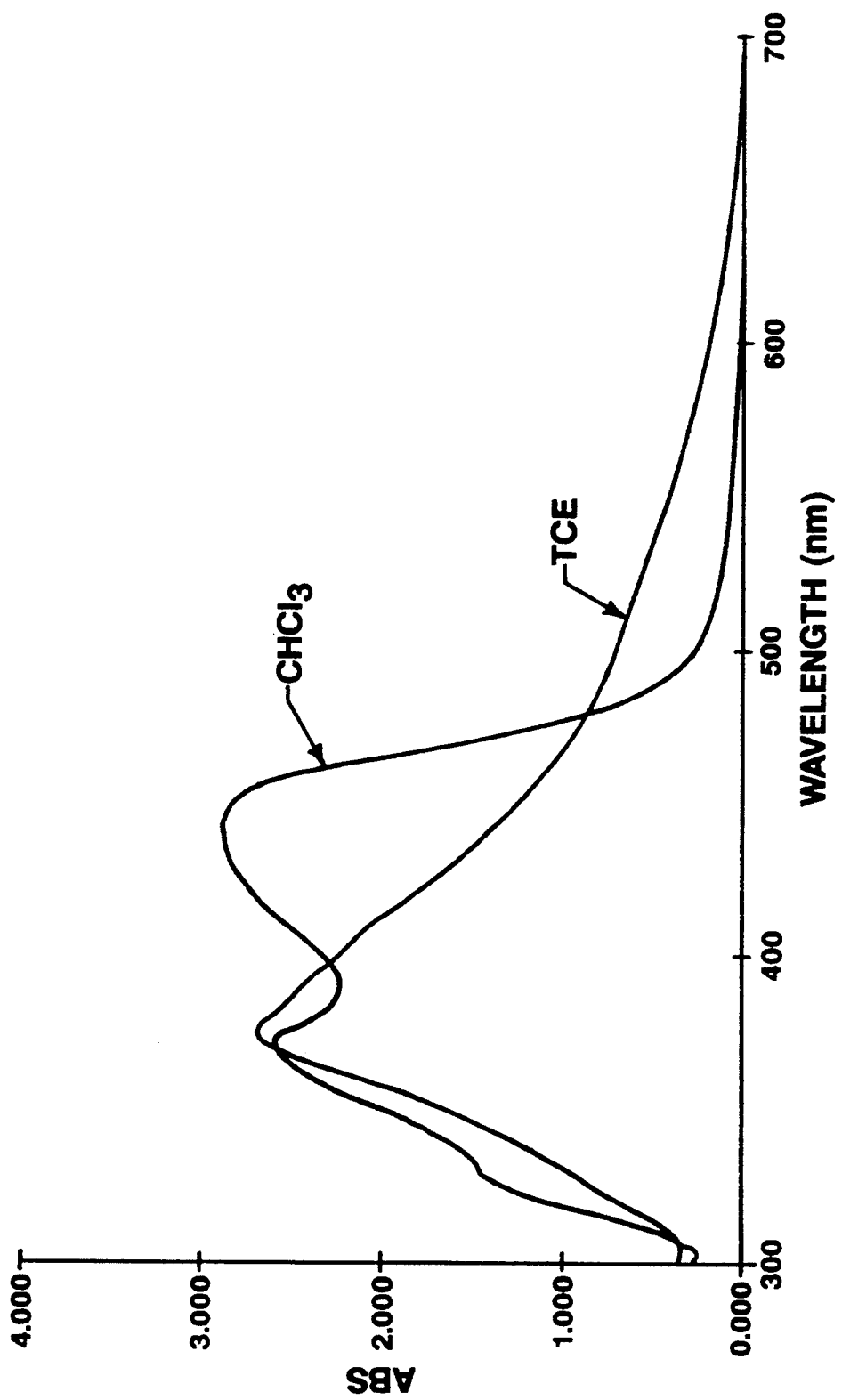
FIGS. 3–5 are the absorption spectra for various halohydrocarbons using various chemistries according to the invention.

Indicator: pyridine (65% v/v)
Base: KTBO (1N)
Modifier: HPP (0.1M)
Solvent: tertiary butyl alcohol The absorption spectrum of FIG. 3 shows a TCE band from 350–480 nm with a peak at 450 nm, and a $CHCl_3$ band from 350–450 nm with a peak at 370 nm. Because of the difference in TCE and chloroform peaks, this chemistry can be used to identify the individual species as well as total TCE and chloroform.

EXAMPLE 2

Figure 4:
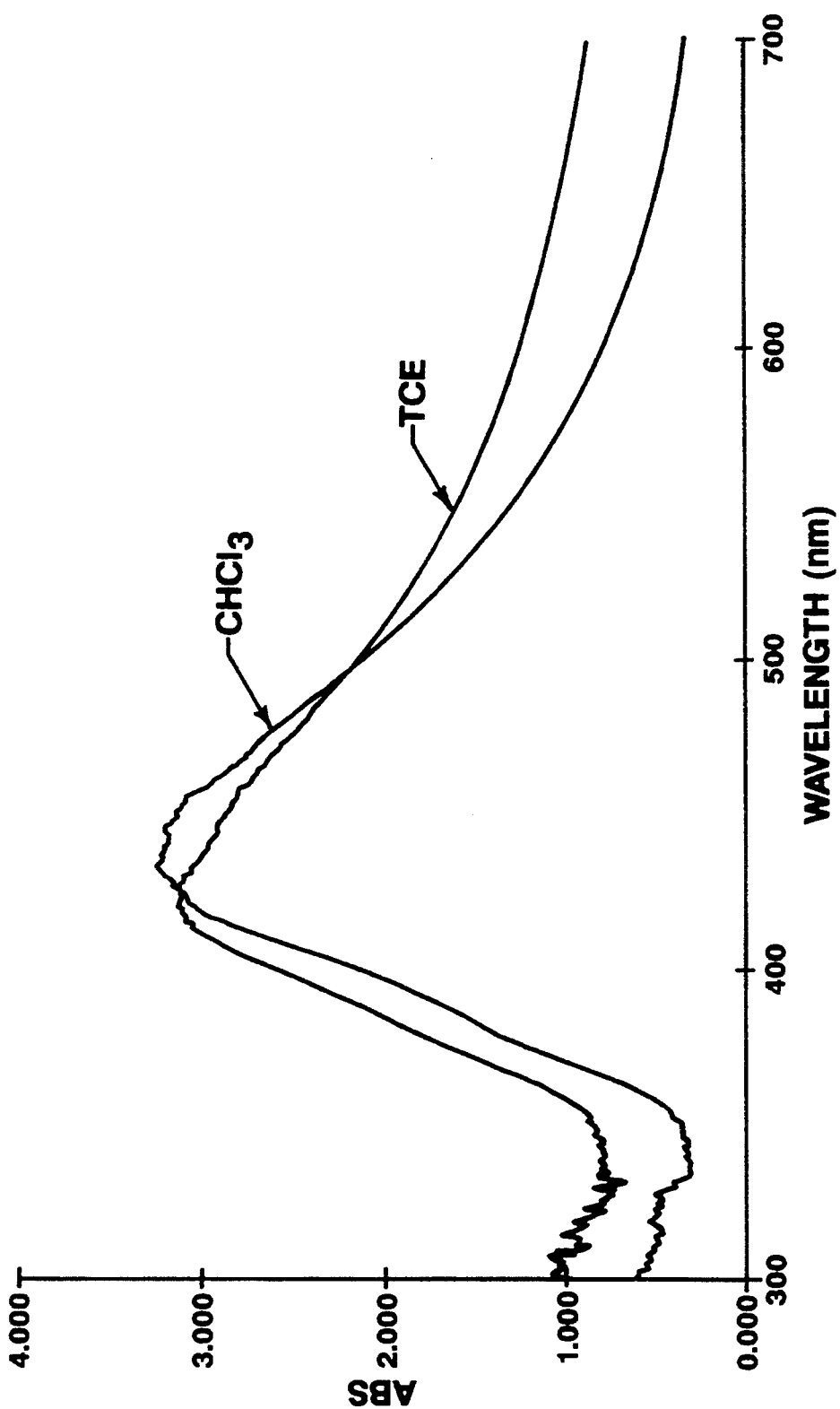

Indicator: 4,4'-bipyridine (5% w/v)
Base: KTBO (1N)
Modifier: HPP (0.1M)
Solvent: tertiary butyl alcohol The absorption spectrum of FIG. 4 shows peaks for TCE and chloroform at about 430 nm so the total can be measured. This chemistry could be placed in a solid state sensor.

EXAMPLE 3

Figure 5:
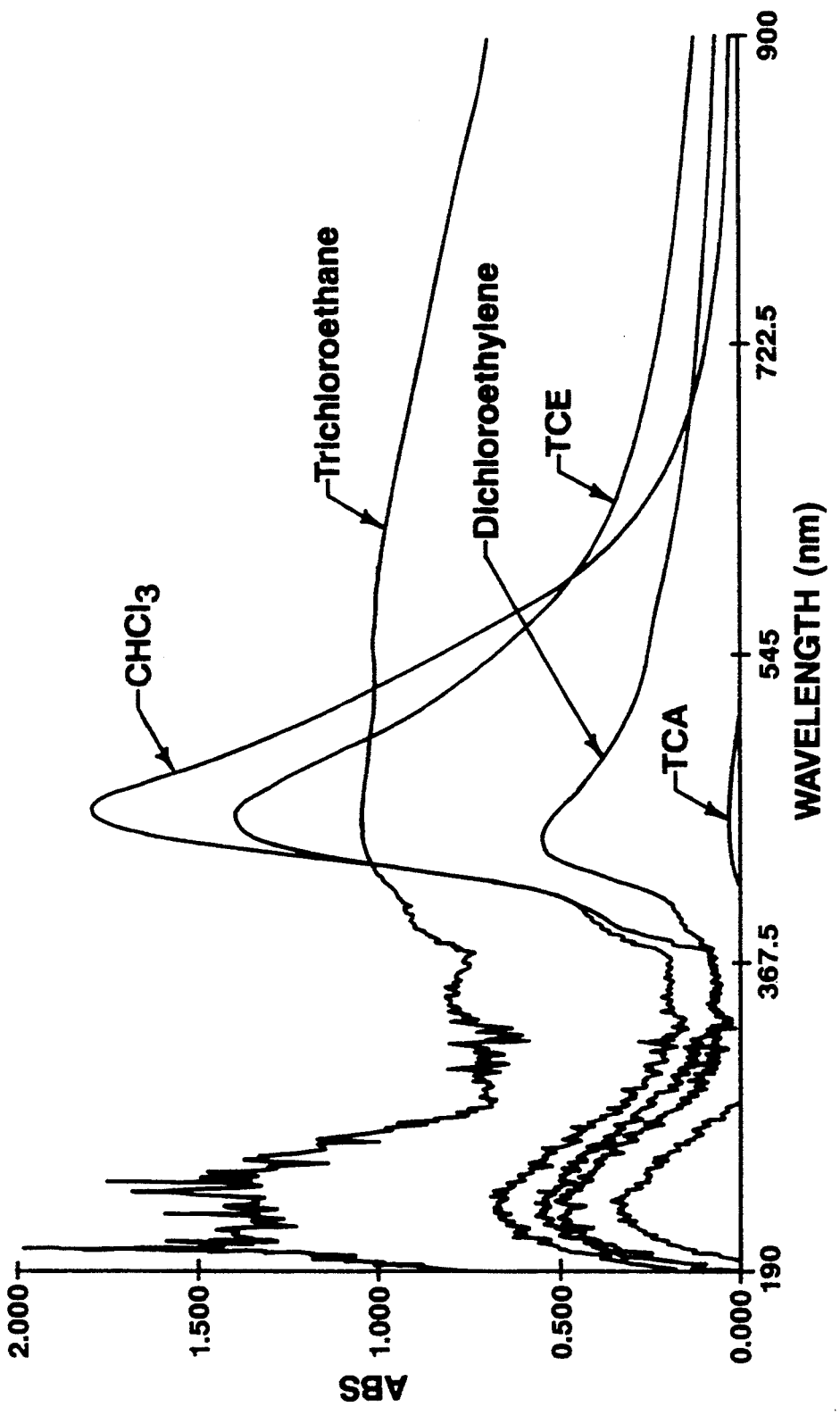

Indicator: 4,4'-trimethylene dipyridine (15% w/v)
Base: KTBO (1N)
Modifier: None
Solvent: tertiary butyl alcohol The absorption spectrum of FIG. 5 shows peaks for TCE and $CHCl_3$ at 450 nm, plus responses to other halohydrocarbons. This chemistry is good for the total halohydrocarbon. This chemistry could also be placed in a solid state sensor.

The chemistry according to the invention generally provides some capability for identifying particular species, e.g., TCE. The chemistry of Example 2 produces a TCE peak that is sufficiently separated from the chloroform peak so that identification is possible. Where necessary, chemometric (multivariate) analysis can be performed to differentiate the peaks. Another way to differentiate the species is to use information about the temporal development of the reaction product. In some cases the formation times for the products with different species may vary greatly. The peaks develop at different times, i.e., reaction rates for different target analytes are different with a particular chemistry. Then even if the peaks overlap in wavelength, they can be temporally separated.

Changes and modification in the specifically described embodiments can be carried out without departing from the scope of the invention which is intended to be limited by the scope of the appended claims.

We claim:

1. A composition for detecting halogenated hydrocarbons, comprising:
   pyridine or a derivative thereof;
   an alkoxide;
   a nonaqueous organic solvent which is less reactive to carbene than the reactivity of pyridine or a derivative thereof.

2. The composition of claim 1 wherein the alkoxide is butoxide, isopropoxide, ethoxide, or a methoxide of sodium, potassium, lithium, ammonium, aluminum or titanium.

3. The composition of claim 1 wherein the solvent is tertiary butyl alcohol, isopropanol, acetonitrile or tetrahydrofuran.

4. The composition of claim 1 wherein the alkoxide is potassium tertiary butoxide and the solvent is tertiary butyl alcohol.

5. A composition for detecting halogenated hydrocarbons, comprising:
   pyridine or a derivative thereof;
   an alkoxide;
   a solid state matrix in which the pyridine or derivative thereof and the alkoxide are embedded.

6. The composition of claim 5 wherein the solid state matrix is a polymer.

7. The composition of claim 1 further comprising:
   a base modifier.

8. The composition of claim 7 wherein the base modifier is a pyrimidine.

9. The composition of claim 8 wherein the pyrimidine is hexahydro pyrimido pyrimidine or hexahydromethyl pyrimido pyrimidine.

10. The composition in claim 7 wherein the base modifier is a nitrogen heterocyclic compound.

11. The composition of claim 1 wherein the pyridine derivative is 4,4'-bipyridine or 4,4'-trimethylene bipyridine.

12. The composition of claim 1 wherein the alkoxide is selected to react with different halogenated hydrocarbon species at different rates so that individual species can be identified by time of formation of a reaction product.

13. The composition of claim 5 wherein the alkoxide is butoxide, isopropoxide, ethoxide, or methoxide of sodium, potassium, lithium, ammonium, aluminum, or titanium.

14. The composition of claim 5 wherein the pyridine or derivative thereof is a substituted pyridine.

15. The composition of claim 5 wherein the solid state matrix is porous glass.

16. A method of detecting halogenated hydrocarbons, comprising:
    contacting a sample with a mixture of pyridine or a derivative thereof and an alkoxide;
    detecting fluorometric or colorimetric changes of a reaction product.

17. The method of claim 16 further comprising embedding the pyridine or derivative thereof and alkoxide in a solid state matrix.

18. The method of claim 16 further comprising mixing the pyridine or derivative thereof and alkoxide in a nonaqueous organic solvent.

* * * * *